US00PP20108P2

(12) United States Plant Patent
Cho

(10) Patent No.: US PP20,108 P2
(45) Date of Patent: Jun. 16, 2009

(54) ***COLOCASIA* PLANT NAMED 'HILO BAY'**

(50) Latin Name: *Colocasia*
Varietal Denomination: Hilo Bay

(76) Inventor: John Cho, 424 Mauna Pl., Kuta, HI (US) 96790

( * ) Notice: Subject to any disclaimer, the term of this patent is extended or adjusted under 35 U.S.C. 154(b) by 0 days.

(21) Appl. No.: 12/006,474

(22) Filed: Jan. 4, 2008

(51) Int. Cl.
*A01H 5/00* (2006.01)

(52) U.S. Cl. ..... Plt./263.1; Plt./226

(58) Field of Classification Search ..... Plt./226, Plt./263.1, 258
See application file for complete search history.

*Primary Examiner*—Annette H Para
*Assistant Examiner*—Louanne C Krawczewicz Myers

(57) ABSTRACT

A new cultivar of *Colocasia* plant named 'HILO BAY' that is characterized by a combination of large, glossy olive green colored, slightly ovate leaves that are ruffled or corrugated in texture and has an undulating leaf margin, dark purple petioles, and produces multiple secondary lateral shoots that are attached to the mother plant on short stolons. In combination these characteristics distinguish 'HILO BAY' from all other varieties of *Colocasia* known to the inventor.

5 Drawing Sheets

Genus: *Colocasia.*
Species: *esculenta.*
Denomination: 'HILO BAY'.

BACKGROUND OF THE INVENTION

The present invention relates to a new and distinct variety of *Colocasia* commonly known as the taro plant or elephant ears. *Colocasia* is grown as a food crop or for use as an ornamental for container or the landscape. The new cultivar is known botanically as *Colocasia esculenta* and will be referred to hereinafter by the cultivar name 'HILO BAY'. 'HILO BAY' is one of is one of five co-pending applications by the inventor relating to new cultivars of *Colocasia.* The other four co-pending applications are titled 'Hawaiian Eye' Plant application Ser. No. 12/006,580, 'Blue Hawaii' Plant application Ser. No. 12/006,576, 'Diamond Head' Plant application Ser. No. 12/006,579, and 'Pineapple Princess' Plant application Ser. No. 12/006,581.

*Colocasia* is a tuberous rooted perennial which is native to tropical Asia and Polynesia. It grows to 1.5–2 m in height from starchy tubers. The leaves of *Colocasia* are heart-shaped and very large in size. The tuberous roots are cooked and eaten as a starchy staple in many tropical areas. It is also grown as ornamental plants for the landscape in warmer climates or as a container plant in colder areas.

The new *Colocasia* variety named 'HILO BAY' is the product of a formal breeding program at Hawaii, Kula. The purpose of the breeding program was to develop new commercial varieties by combining attributes not found in currently commercially available varieties.

'HILO BAY' is a seedling selection from the controlled pollination between the female parent '2000-110' (unpatented) and male parent '2000-177' (unpatented). The female parent '2000-110' was selected from the progeny of a genetic cross between breeding hybrid line '(T×NW21)' (unpatented) and breeding hybrid line 'T12' (unpatented). The male parent '2000-177' was selected from a genetic cross between *Colocasia* 'Putih' (unpatented) and *Colocasia* 'PH21' (unpatented). Initially designated as '2005-5', 'HILO BAY' was derived from a single plant selected in 2005.

The new variety 'HILO BAY' has very large glossy olive green slightly ovate leaves that are ruffled or corrugated in texture with undulating leaf margins and with a light purple vertical vein. 'HILO BAY' produces uniform dark purple petioles. The leaves are similar in size compared to its male parent and 2 to 3 times larger than its female parent The male parent, '2000-177', exhibits a smaller glossy green leaves with irregular purple blotches with a smooth margin. The petioles are a light green to a light purple color with dark purple streaks. The female parent, '2000-110' exhibits smaller green leaves with a purple spot on the upper leaf surface at the point of leaf and petiole attachment and a smooth margin. The petioles are of a light green color. In these aspects, this new variety differs from its parents.

The closest comparison variety known to the inventor is 'Fontanesii' (unpatented), its closest commercial variety. HILO BAY produces glossy olive green leaves that are ruffled or corrugated in texture and has undulating leaf margin compared to 'Fontanesii' which exhibits a glossy green smooth leaf with a smooth margin. 'HILO BAY' produces uniform dark purple petioles similar in color compared with 'Fontanesii'. 'HILO BAY' produces secondary lateral shoots that are attached to the mother plant on short stolons as compared with 'Fontanesii' that produces secondary lateral shoots on long stolons.

Asexual propagation of hulis of 'HILO BAY' began in 2005 in Hawaii by the inventor using huli propagation whereby the apical shoots are separated from the plant by cutting the shoot at the top of the corm immediately above the newest leaf scar and planted. Evaluation in field and pot studies have shown the unique features of 'HILO BAY' to be stable, uniform, and reproduces true to type in successive generations of asexual propagation.

SUMMARY OF THE INVENTION

The following traits have been repeatedly observed and represent the distinguishing characteristics of the new *Colo-*

*casia* variety named 'HILO BAY'. In combination these traits set 'HILO BAY' apart from all other varieties of *Colocasia* known to the inventor. 'HILO BAY' has not been tested under all possible conditions and phenotypic differences may be observed with variations in environmental, climatic and cultural conditions, however, without any variance in genotype:

1. 'HILO BAY' exhibits large slightly ovate leaves that are ruffled or corrugated in texture and has an undulating leaf margin.
2. The leaves of 'HILO BAY' are olive green in color with a light purple vertical vein.
3. The surface of the leaves of 'HILO BAY' is glossy.
4. 'HILO BAY' has dark purple petioles.
5. 'HILO BAY' produces secondary lateral shoots that are attached to the mother plant on short stolons.

BRIEF DESCRIPTION OF THE DRAWINGS

The accompanying color drawings

Figure 1:
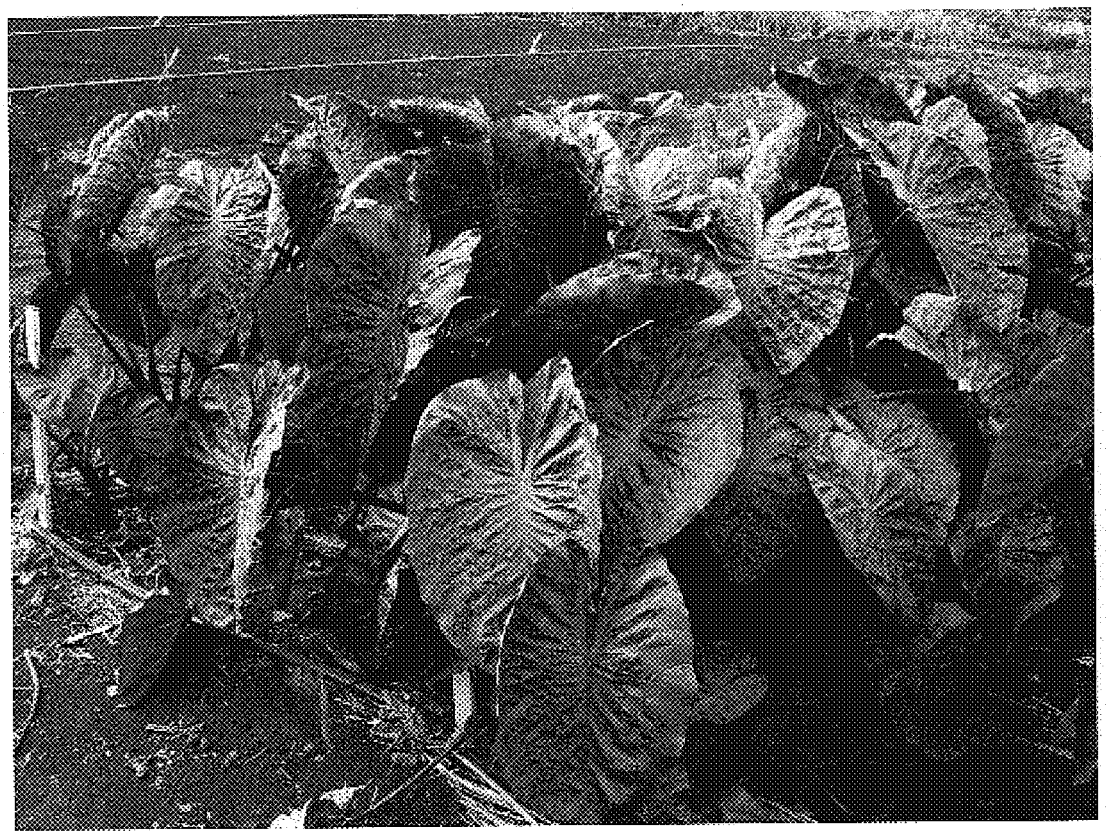
FIGS. 1 to 6 illustrate the overall appearance of 'HILO BAY' showing the colors as true as it is reasonably possible to obtain in colored reproductions of this type. Colors in the drawing may differ from the color values cited in the detailed botanical description, which accurately describe the actual colors of the new variety 'HILO BAY'.

The drawing labeled as FIG. 1 shows 'HILO BAY' grown from a huli after approximately 3 months.

Figure 2:
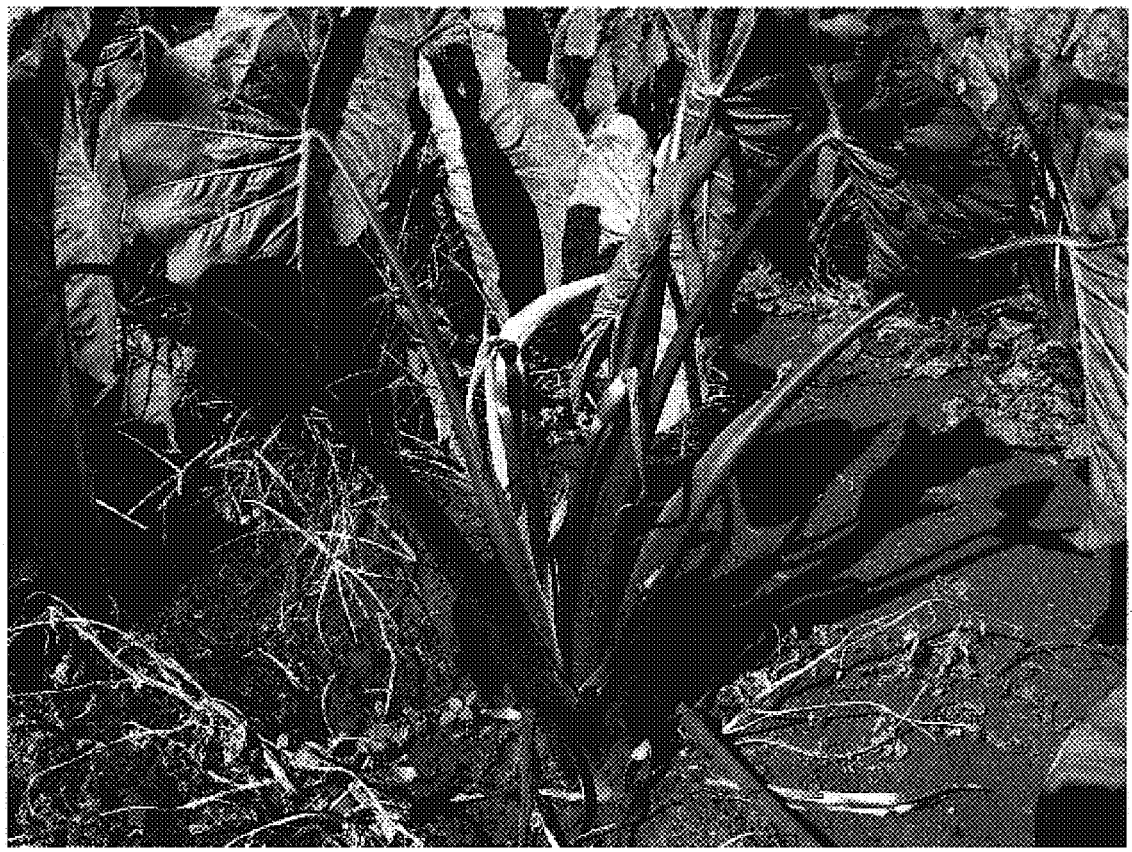

The drawing labeled FIG. 2 illustrates purple colored petioles of 'HILO BAY'.

Figure 3:
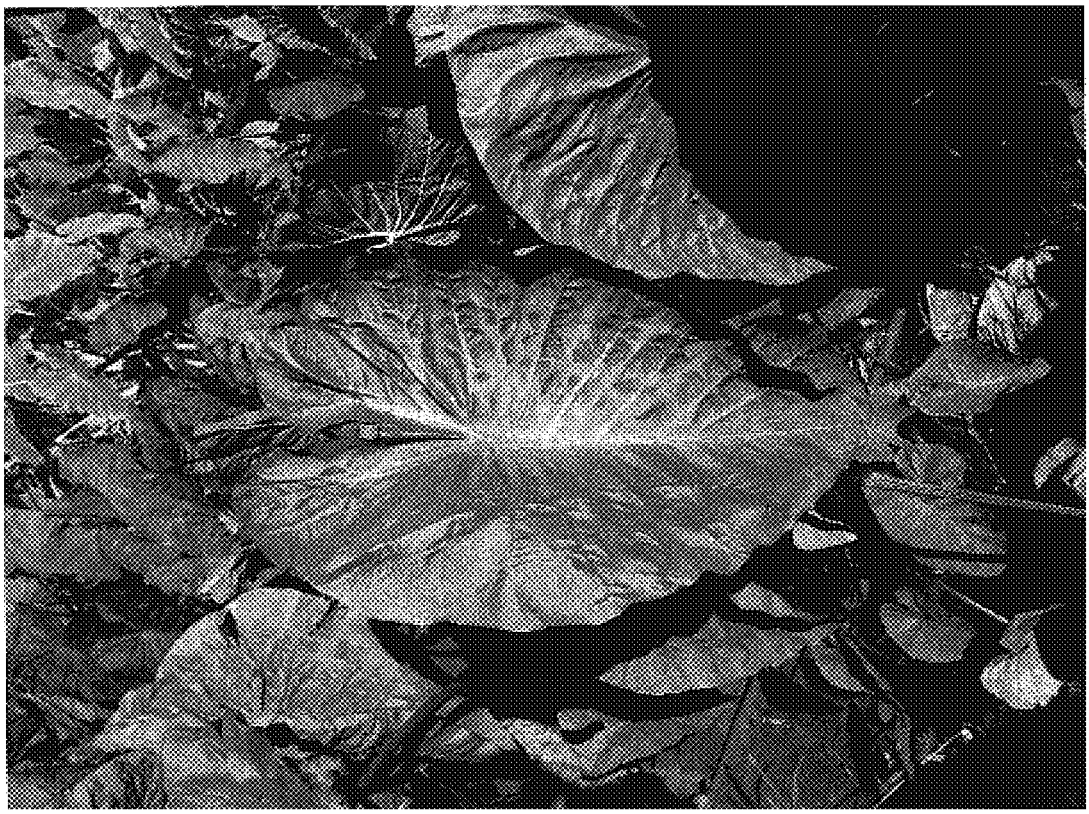

The drawing labeled as FIG. 3 illustrates the ovate 'HILO BAY' mature leaf blade whose lamina is a glossy olive green.

Figure 4:
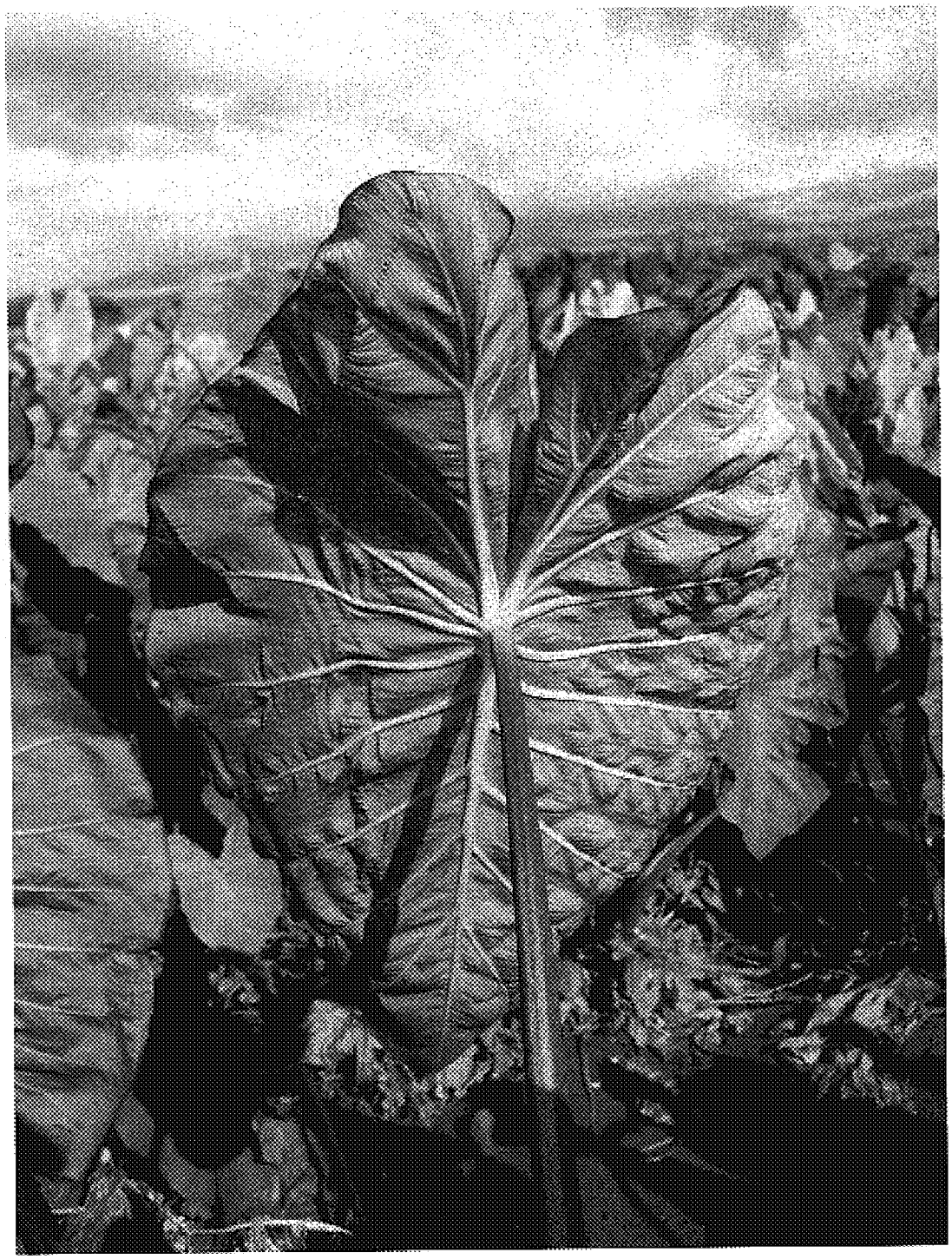

The drawing labeled as FIG. 4 shows the underside of a mature leaf of 'HILO BAY' with the green lamina and slightly purple venation.

Figure 5:
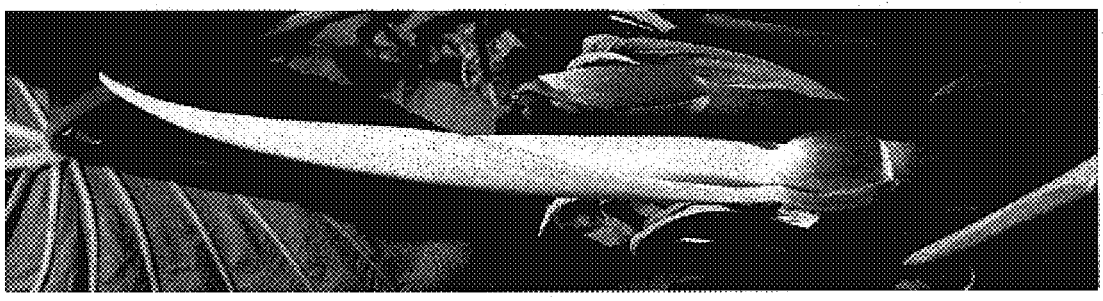

The drawing labeled as FIG. 5 shows spathe or sheath that encloses the spadix of 'HILO BAY' (drawing is sideways to accommodate page size).

Figure 6:
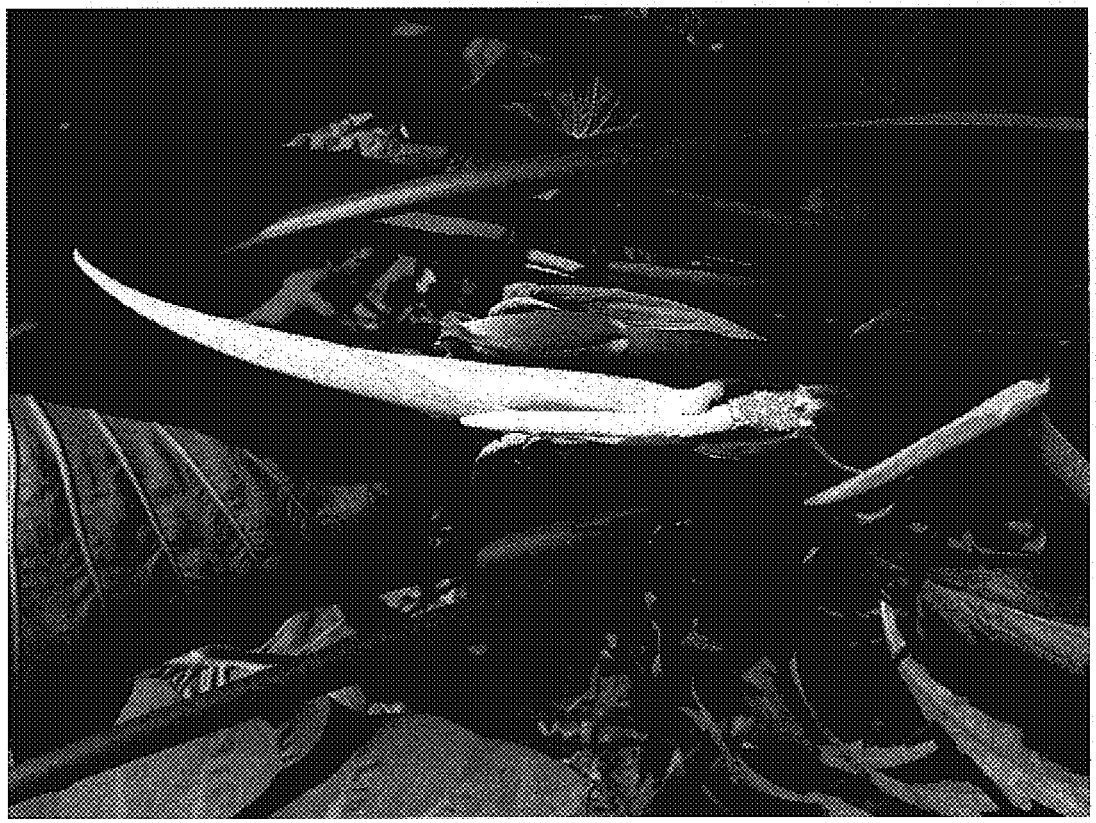

The drawing labeled as FIG. 6 shows the inflorescence or spadix of 'HILO BAY' (drawing is sideways to accommodate page size).

All drawings have been made from plants which were approximately 5 months old from a division and which have been grown out-of-doors. No growth regulators have been applied.

BOTANICAL DESCRIPTION OF THE PLANT

The following is a detailed description of the new *Colocasia* plant named 'HILO BAY'. Data was collected from plants that were 3–6 months of age grown outside in Kula, Hi. as indicated. The color determinations are in accordance with the 2001 edition of The Royal Horticultural Society Colour Chart, London, England, except where general color terms of ordinary dictionary significance are used. The growing requirements are similar to other *Colocasia*.

Botanical classification:
*Genus.*—*Colocasia.*
*Species.*—*esculenta.*

Denomination: 'HILO BAY'.

Common name: Taro or elephant ears.

Plant use: Food, container or landscape plant.

Cultural requirements: Cultural requirements are well draining soil or growing media, full sun to partial shade.

Root system: Fibrous.

Plant vigor: Vigorous.

Plant growth rate: Rapid. At temperatures above 20 Celsius, a new leaf develops and is fully expanded every 10 days.

Parentage:
*Female parent.*—'2000-110'.
*Male parent.*—'2000-177'.

Plant description: The plant has 9-to 11 suckers attached to the mother plant on short stolons. A "mother plant" is the plant material which is first introduced into the soil to begin production. Typically, this plant material contains part of the huli and 2–3 leaf blades. This produces a "mother corm" which produces lateral shoots called 'cormels' which give rise to daughter plants. Daughter plants begin to appear above soil level about 2–3 months after planting of the mother plant.

Plant dimensions: 100 cm to 110 cm in height and 112 cm to 142 cm in width.

Plant hardiness: USDA Zone 7.

Propagation: Propagation is accomplished by huli propagation.

Time to develop daughter plants: Appear above soil around 2–3 months after planting.

Crop time: 1.5 to 2.5 months.

Pest or disease susceptibility and resistance: No more or less susceptible to disease or pests than other cultivars.

Foliage:
*Number.*—On average, a 4–10 month old mother plant maintains 6–7 functional leaves at a time, each new leaf is produced approximately every 10 days until the corm matures.
*Petioles.*—Length: Up to 117 cm in length. Width: 11 mm (just below attachment to lamina)×22 mm (at the upper sinus)×35 mm (at the middle of the sinus). Color: N186C. Sap color: Colorless.
*Leaf.*—Dimensions at maturity (5–6 months old): 61 cm in length and 38 cm in width. Aspect: Erect with apex down. Shape: Sagittate, slightly ovate lamina. Margins: Entire, undulating. Apex: Pointed. Base: Peltate. Lamina appendages: Absent. Attachment: Piko, small in size, colored N186D. Leaf sheaf: Open. Texture (adaxial surface): Smooth, appears glossy and gently folded. Texture (abaxial surface): Smooth, appears matte with many fold lines. Leaf color (adaxial surface): 147A when young changing to 186B when older. Leaf color (abaxial surface): 148A. Venation: Palmate. Veins: Three principal veins radiating from the piko. The largest a midrib extending from the piko to the tip of the lamina with up to 11 pairs of secondary veins radiating from it. Vein color (adaxial surface): N186D. Vein color (abaxial surface): N186D.

Flowers and reproductive organs: The inflorescence arises from the leaf axils. The inflorescence is made up of a short peduncle, a spadix, and spathe. The spadix is botanically a spike, with a fleshy central axis to which the small sessile flowers are attached. The spadix is 115 mm to 125 mm long, with female flowers at the base, male flowers towards the tip, and sterile flowers in between, in the region compressed by the neck of the spathe. The extreme tip or appendage of the spadix has no flowers at all. The spathe is a large yellowish bract, 250 mm to 260 mm long, which sheathes the spadix. The lower part of the spathe is purple (N186C) in color and wraps tightly around the spadix and completely occludes the female flowers from view. The top portion of the spathe is yellow (13C) in color and is rolled inward at the apex, but is open on one side to reveal the male flowers on the spadix. The top and bottom portions of the spadix are separated by a narrow neck region, corresponding to the region of the sterile flowers on the spadix.

It is claimed:

1. A new and distinct cultivar of *Colocasia* plant named 'HILO BAY' as described and illustrated herein.

* * * * *

UNITED STATES PATENT AND TRADEMARK OFFICE

CERTIFICATE OF CORRECTION

PATENT NO. : PP20,108 P2
APPLICATION NO. : 12/006474
DATED : June 16, 2009
INVENTOR(S) : John Cho It is certified that error appears in the above-identified patent and that said Letters Patent is hereby corrected as shown below:

On Column 1, line 1, please insert the following header and paragraph:

--Statement of Government Interest

This invention was made with Government support under Grant No. 2001-31100-06015/HAW914H awarded by the U.S. Department of Agriculture. The Government has certain rights in this invention.--

Signed and Sealed this
Twenty-second Day of November, 2011

David J. Kappos

David J. Kappos
*Director of the United States Patent and Trademark Office*